(12) United States Patent
Hasenoehrl et al.

(10) Patent No.: US 8,475,817 B2
(45) Date of Patent: Jul. 2, 2013

(54) CLEANSING ARTICLES FOR SKIN OR HAIR

(75) Inventors: Erik John Hasenoehrl, Loveland, OH (US); Sabrina Turacchio, Manoppello (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/888,124

(22) Filed: Jul. 31, 2007

(65) Prior Publication Data
US 2008/0075748 A1     Mar. 27, 2008

Related U.S. Application Data

(60) Provisional application No. 60/834,669, filed on Jul. 31, 2006.

(51) Int. Cl.
*A61K 31/00*     (2006.01)

(52) U.S. Cl.
USPC .......................................................... 424/402

(58) Field of Classification Search
None
See application file for complete search history.

(56) References Cited

U.S. PATENT DOCUMENTS

| | | |
|---|---|---|
| 3,929,678 A | 12/1975 | Laughlin et al. |
| 4,142,334 A | 3/1979 | Kirsch et al. |
| 4,557,853 A | 12/1985 | Collins |
| 4,601,938 A | 7/1986 | Deacon et al. |
| 4,891,227 A | 1/1990 | Thaman et al. |
| 4,891,228 A | 1/1990 | Thaman et al. |
| 5,069,897 A | 12/1991 | Orr |
| 5,213,588 A | 5/1993 | Wong et al. |
| 6,238,767 B1 * | 5/2001 | McCormack et al. .......... 428/99 |
| 6,280,757 B1 | 8/2001 | McAtee et al. |
| 6,361,784 B1 * | 3/2002 | Brennan et al. ............... 424/402 |
| 6,491,937 B1 * | 12/2002 | Slavtcheff et al. ............ 424/402 |
| 8,017,145 B2 | 9/2011 | Hart et al. |
| 2003/0031703 A1 | 2/2003 | McMeekin et al. |
| 2003/0228351 A1 * | 12/2003 | Hasenoehrl et al. .......... 424/443 |
| 2003/0228352 A1 | 12/2003 | Hasenoehrl et al. |
| 2004/0242097 A1 * | 12/2004 | Hasenoehrl et al. ............ 442/59 |
| 2005/0003721 A1 * | 1/2005 | Greulich et al. ................ 442/67 |
| 2006/0177488 A1 | 8/2006 | Caruso et al. |

FOREIGN PATENT DOCUMENTS

| | | |
|---|---|---|
| EP | 0 404 500 A2 | 12/1990 |
| EP | 1283019 | * 12/2003 |
| WO | WO 02/056741 A1 | 7/2002 |

OTHER PUBLICATIONS

U.S. Appl. No. 29/263,935, filed Jul. 31, 2006, Roberts et al.
The Encyclopedia Americana, vol. 11, pp. 147-153 and vol. 26, pp. 566-581 (1984).
The Merck Index, Tenth Edition, Entry 7048, p. 1033 (1983).

(Continued)

*Primary Examiner* — Brian Gulledge
(74) *Attorney, Agent, or Firm* — Mark Charles; Carl J. Roof

(57) ABSTRACT

The present invention relates to substantially dry personal cleansing articles useful for cleansing the skin or hair. These articles are used by the consumer by wetting the substantially dry article with water and then rubbing the article against the skin or hair. The article comprises a water-insoluble substrate having non-fibrous polymeric raised areas on at least one surface of said water insoluble substrate that are formed of a polymeric material having a Shore A hardness of no more than about 80, and a lathering surfactant releasably associated with the substrate. Preferably, the articles of the present invention further comprise a conditioning component.

16 Claims, 1 Drawing Sheet

OTHER PUBLICATIONS

The Merck Index, Tenth Edition, Entry 7047, p. 1033 (1983).
Schindler, Drug. Cosmet. Ind., 89, 36-37, 76, 78-80, 82 (1961).
International Cosmetic Ingredient Dictionary, Fifth Edition, vol. 1, p. 537 (1993).
International Cosmetic Ingredient Dictionary, Fifth Edition, vol. 1, p. 415-417 (1993).
International Search Report PCT/IB2007/053023 mailed Jan. 21, 2008, 11 pages.

* cited by examiner

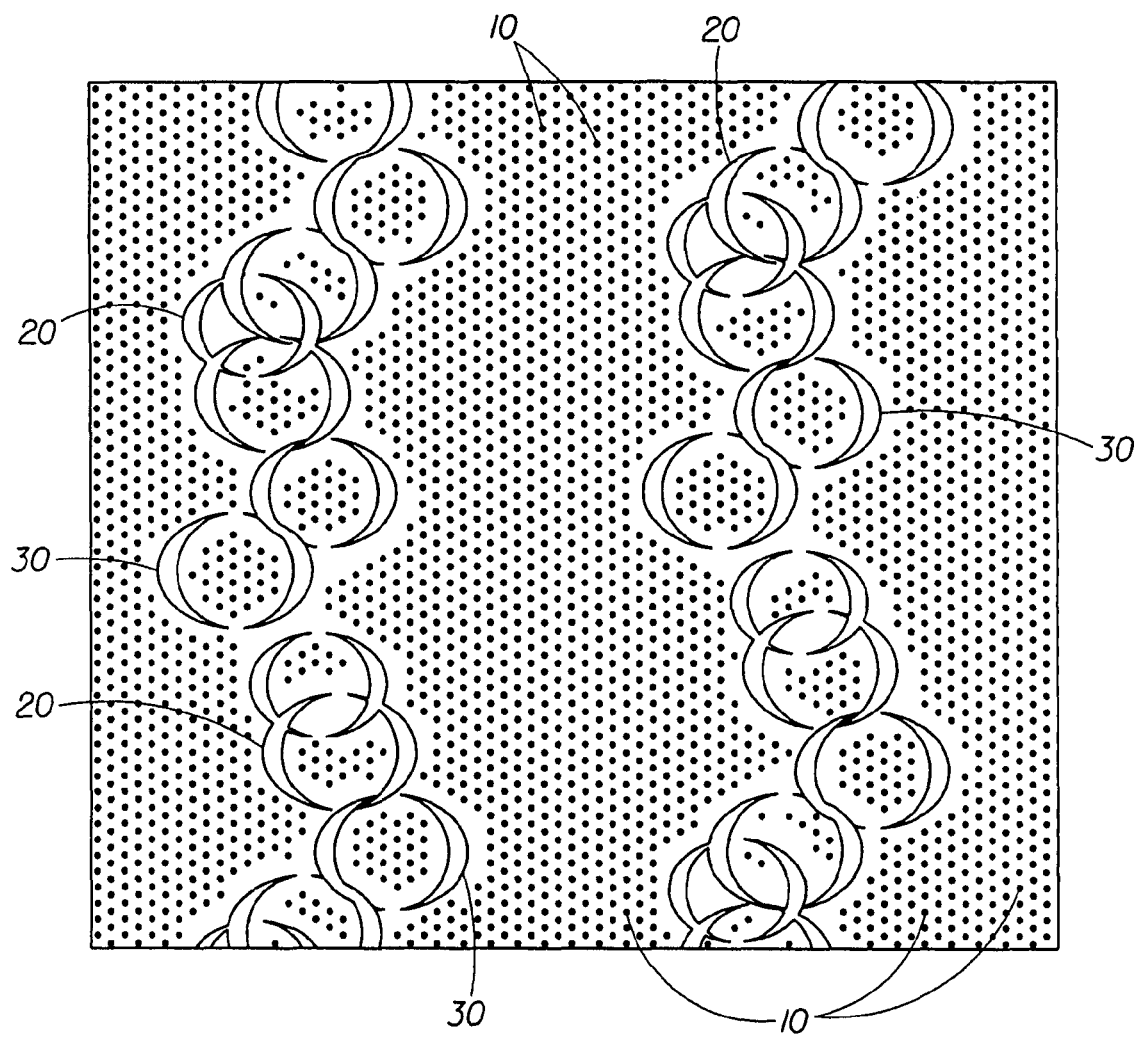

CLEANSING ARTICLES FOR SKIN OR HAIR

CROSS REFERENCE TO RELATED APPLICATION

This application claims the benefit of U.S. Provisional Application Ser. No. 60/834,669, filed Jul. 31, 2006.

TECHNICAL FIELD

The present invention relates to disposable personal cleansing articles useful for cleansing, and optionally conditioning, the skin or hair, and more particularly to a disposable, cleansing article comprising a water insoluble substrate and a lathering surfactant component wherein the substrate comprises non-fibrous polymeric raised areas on at least one side of the substrate. These cleansing articles are typically used by the consumer by wetting the article with water and thereafter forming lather by rubbing the article against itself and/or against skin or hair.

BACKGROUND OF THE INVENTION

Personal cleansing products have traditionally been marketed in a variety of forms such as bar soaps, creams, lotions, and gels. These cleansing formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use. Personal cleansing products are frequently used with, or marketed in the form of, articles that employ a substrate or other implement that carries a cleansing material or is used to deliver a cleansing material to the skin or hair.

Personal cleansing cloths have become a popular cleansing product among consumers. Such products generally include a water insoluble substrate material that is impregnated with a cleansing composition. Some cloths further contain conditioning agents that moisturize the skin and/or hair, in addition to cleansing the skin and/or hair. The personal cleansing cloths are typically available as either wet or substantially dry cleansing cloths. Wet cleansing cloths are packaged to maintain the cloths in pre-moistened form and the cloths are then simply removed from its packaging and wiped against the skin and/or hair to cleanse the skin and/or hair. Substantially dry cleansing cloths are available that require a consumer to wet the cloths with water, manipulate the cloths to generate lather, and then wipe the cloths against the skin and/or hair to cleanse the skin and/or hair.

Attempts have been made to improve the cleansing and exfoliation performance of such cloths, primarily wet cleansing cloths, by incorporating raised areas on the cloths usually in the form of small discrete dots formed by polymeric or plastic-type materials. However, these products have not been well-received by many consumers who find them to be too harsh and abrasive on the skin.

There has thus been a desire to develop a personal cleansing cloth that provides effective cleansing and exfoliation, while not being too harsh or abrasive on the skin and/or hair.

SUMMARY OF THE INVENTION

The present invention relates to substantially dry personal cleansing articles, especially useful for cleansing facial skin, which comprise: (a) a water-insoluble substrate comprising non-fibrous polymeric raised areas on at least one surface of said water insoluble substrate, wherein said non-fibrous polymeric raised areas are formed of a polymeric material having a Shore A hardness of no more than about 80; and (b) from about 0.5% to about 250%, by weight of said substrate, of a lathering surfactant releasably associated with said substrate. The cleansing articles described herein optionally contain one or more water-soluble and/or water-insoluble conditioning agents in addition to the lathering surfactant component.

The present invention also relates to processes for manufacturing cleansing articles of the configuration described herein. Also, the present invention provides methods for cleansing, and optionally conditioning, the skin or hair using the articles described herein.

BRIEF DESCRIPTION OF THE DRAWINGS

FIG. 1 is a top view of one embodiment of a personal cleansing article of the present invention comprising non-fibrous polymeric raised areas, wherein the non-fibrous polymeric raised areas comprise a plurality of small continuous raised areas and a plurality of large continuous raised areas.

DETAILED DESCRIPTION OF THE INVENTION

By a "lathering surfactant" is meant a surfactant, which when combined with water and mechanically agitated generates a foam or lather.

The term "lathering product" or "lathering article," as used herein, means that the product or article contains enough of the surfactants described herein that it can generate at least 30 ml of Lather Volume, as described herein in the Lather Volume Test. These Lather Volume measurements are conducted with a medium hardness water (8-10 grains per gallon) at 35° C. (95° F.).

The terms "disposable" or "single use", are used herein in their ordinary sense to mean an article that is disposed or discarded after one typical usage event.

The term "water-activated," as used herein, means that the present invention is presented to the consumer in a form to be used after it is wetted with water. It is found that these articles produce a lather or are "activated" by contacting them with water and then further subjecting the article to mechanical forces, such as rubbing.

The term "substantially dry," as used herein, means that prior to use the article is substantially free of water and generally feels dry to the touch. Thus, the articles of the present invention will generally comprise less than about 20%, by weight of the article, of water, preferably less than about 10%, by weight of the article, of water, and more preferably less than about 5%, by weight of the article, of water, the forgoing measured in a dry environment, e.g., low humidity. One of ordinary skill in the art would recognize that the water content of an article such as in the present invention can vary with the relative humidity of the environment.

Water Insoluble Substrate

The products of the present invention comprise a water insoluble substrate having at least one cleansing surface. By "water insoluble" is meant that the substrate does not dissolve in or readily break apart upon immersion in water. The water insoluble substrate is the implement or vehicle for delivering the lathering surfactant and optionally the conditioning component of the present invention to the skin or hair to be cleansed and conditioned. Without being limited by theory, it is believed that the substrate, by providing mechanical forces and agitation provides a lather generating effect and also aids in the deposition of the conditioning component.

A wide variety of materials can be used as the substrate, such as nonwoven substrates. The term "nonwoven" refers to fabrics made of fibers held together by interlocking or interfiber bonding which are not woven, knitted, felted, or the like. However, the nonwoven substrate referred to herein may comprise fibers that are initially substantially unbonded which are subsequently bonded to each other. A nonwoven substrate is comprised of fibers which are not woven into a fabric but rather are formed into a sheet, mat, or pad layer. The fibers can either be random (i.e., randomly aligned) or they can be carded (i.e., combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," Nonwoven World (1987); The Encyclopedia Americana, vol. 11, pp. 147-153, and vol. 26, pp. 566-581 (1984); U.S. Pat. No. 4,891,227, to Thaman et al., issued Jan. 2, 1990; and U.S. Pat. No. 4,891,228.

The substrate of the present invention typically has a basis weight of between 15 to about 100 grams per square meter, preferably from about 30 to about 85 grams per square meter, and more preferably from about 45 to about 70 grams per square meter ("gsm").

Methods of making nonwoven substrates are well known in the art. Generally, these nonwoven substrates can be made by air-laying, water-laying, meltblowing, coforming, spinbonding, or carding processes in which the fibers or filaments are first cut to desired lengths from long strands, passed into a water or air stream, and then deposited onto a screen or belt through which the fiber-laden air or water is passed. The resulting web of fibers, regardless of its method of production or composition, is then subjected to at least one of several types of bonding operations to anchor the individual fibers together to form a self-sustaining web. In the present invention the nonwoven substrate can be prepared by a variety of processes including hydroentanglement, thermally bonding or thermo-bonding, and combinations of these processes. Moreover, the substrates used in the present invention can consist of a single layer or multiple layers. In addition, a multilayered substrate can include films and other nonfibrous materials.

The substrate can be made into a wide variety of shapes and forms including flat pads, thick pads, thin sheets, ball-shaped implements, irregularly shaped implements, and having sizes ranging from providing a cleansing surface area of at least about 5 cm$^2$. The exact size will depend upon the desired use and product characteristics. Especially convenient are square, circular, rectangular, or oval substrates having a cleansing surface area of from about 6 cm$^2$ to 1000 cm$^2$, preferably from about 65 cm$^2$ to about 775 cm$^2$, and more preferably from about 150 cm$^2$ to about 400 cm$^2$ and a thickness of from about 1 mil to about 500 mil, preferably from about 5 mil to about 250 mil, and more preferably from about 10 mil to about 100 mil.

The water insoluble substrate of the present invention can comprise one or more layers of material, preferably nonwoven material. In one embodiment, the substrate is a single layer, nonwoven, hydroentangled substrate.

The water insoluble substrate of the present invention can be apertured or non-apertured. The substrate is preferably non-apertured since it is easier to apply the non-fibrous polymeric raised areas of the present invention to a non-apertured substrate.

Non-Fibrous Polymeric Raised Areas

The personal cleansing articles of the present invention further comprise non-fibrous polymeric raised areas on at least one side of the water insoluble substrate. The non-fibrous polymeric raised areas provide texture for effective cleansing and exfoliation during use of the personal cleansing article of the present invention.

The non-fibrous polymeric raised areas are made of a polymeric material that has a Shore A hardness value of no more than about 80, preferably from about 40 to about 80. The Shore A hardness value of a material is measured according to standard methods described in ASTM 2240. A variety of polymeric materials can be utilized, including hot melt coatings, natural rubber, synthetic rubber, polyethylene, polypropylene, ethylene vinyl acetate, thermoplastic elastomers, and the like.

Nonlimiting examples of suitable polymeric materials include: ELVAX 210 which is an ethylene vinyl acetate copolymer resin available from DuPont and having a Shore A hardness of about 60; VESTOPLAST 703 which is a propene-rich amorphous poly-alpha-olefin available from Degussa and having a Shore A hardness of about 70; and ESCORENE ULTRA EVA MV 02528EH2 which is a copolymer of ethylene and vinyl acetate available from ExxonMobil Chemical Company and having a Shore A hardness of about 50.

The non-fibrous polymeric raised areas provide texture to the cloth, without having to utilize a nonwoven substrate that has texture due to raised fibrous areas which can result from various ways of processing nonwoven materials. Such textured nonwoven materials with raised fibrous areas, however, tend to be rather expensive due to the processing required to achieve such textured materials. In utilizing the non-fibrous polymeric raised areas according to the present invention, much more common, and less expensive, nonwoven materials can be utilized to create a personal cleansing article that still has texture for effective cleansing.

The non-fibrous polymeric raised areas can also enable a variety of designs and patterns to be produced on the surface(s) of the substrate. In this respect, the polymeric material used to form the non-fibrous polymeric raised areas can be mixed, or otherwise combined, with a various colorants or pigments to create colored designs and patterns on the personal cleansing articles. Suitable colorants are commercially available from Standrich.

The non-fibrous polymeric raised areas will have an average height, as measured from the cleansing surface of the substrate to the top of the non-fibrous polymeric raised areas, of at least about 0.01 mm, preferably from about 0.05 mm to about 1 mm, and more preferably from about 0.1 mm to about 0.5 mm. If the non-fibrous polymeric raised areas are applied to the substrate via a gravure coating process, the height of the raised areas corresponds to the pattern depth on the gravure roll. In this respect, each raised area can have the same height or can have varying heights, depending on how the pattern depth is adjusted on the gravure roll for each raised area.

The non-fibrous polymeric raised areas preferably comprise a plurality of small continuous raised areas and a plurality of large continuous raised areas. The small continuous raised areas tend to aid in skin exfoliation, while the large continuous raised areas tend to aid in depositing conditioning agents, when present, on the skin and/or hair, especially when the conditioning agents are added to the substrates after the non-fibrous polymeric raised areas are added to the substrates.

The small continuous raised areas are typically in the form of a variety of geometric shapes, including circular dots, squares, diamonds, triangles, and other geometric shapes. The small continuous raised areas each have a surface area of from about 0.1 $mm^2$ to 10 $mm^2$, preferably from about 0.5 $mm^2$ to about 5 $mm^2$, and more preferably from about 0.8 $mm^2$ to about 3 $mm^2$.

The large continuous raised areas can be in the form of a variety of patterns, including geometric shapes as well as more irregular patterns, which are larger than the small continuous raised areas described above. The large continuous raised areas each have a surface area of greater than 10 $mm^2$ to about 5,000 $mm^2$, preferably from about 15 $mm^2$ to about 1,000 $mm^2$, and more preferably from about 50 $mm^2$ to about 500 $mm^2$.

FIG. 1 shows one non-limiting embodiment of a non-fibrous polymeric raised area pattern of the present invention that comprises a plurality of small continuous raised areas 10 and a plurality of large continuous raised areas 20, 30. In this embodiment, the small continuous raised areas 10 are circular dots having a surface area of approximately 0.8 $mm^2$ each. The large continuous raised areas 20, 30 are a series of "crescent moon" shapes, wherein some of the "crescent moon" shapes overlap each other to create large continuous raised areas 20 having a larger surface area versus other large continuous raised areas 30 that have only one "crescent moon" shape that does not overlap or otherwise connect to other "crescent moon" shapes. In this embodiment, the large continuous raised areas each have a surface area of from about 50 $mm^2$ to about 500 $mm^2$.

The non-fibrous polymeric raised areas can be applied to a cleansing surface of the substrate via a number of different processes known in the art. Suitable processes include spraying, printing (e.g., flexographic printing or screen printing), coating (e.g., gravure coating or slot coating), extrusion, and the like. Preferably, the non-fibrous polymeric raised areas are applied to the substrate via a gravure coating process.

Lathering Surfactant

Besides the water-insoluble substrate comprising non-fibrous polymeric raised areas, the articles of the present invention also comprise one or more lathering surfactants which are releasably associated with the water-insoluble substrate. Thus the lathering surfactants can be added onto or impregnated into the substrate. Generally this will be done prior to the point of use of the article, i.e., the surfactants will be combined with the article and the article dried before the article is ultimately wetted for use. Preferred articles of the present invention comprise a sufficient amount of one or more lathering surfactants such that the articles are capable of generating at least 30 ml of Lather Volume (medium hardness water at 35° C. (95° F.) according to the Lather Volume Test described below.

Generally the articles will contain from about 0.5% to 250%, by weight of the substrate, of a lathering surfactant that is releasably associated with the substrate. Preferably, the articles of the present invention comprise from about 0.5% to about 50%, more preferably from about 0.75% to about 30%, and most preferably from about 1% to about 20%, based on the weight of the water insoluble substrate, of a lathering surfactant component.

By a lathering surfactant is meant a surfactant, which when combined with water and mechanically agitated generates a foam or lather sufficient to cause the article, as a whole, to provide a lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lathering surfactants, amphoteric lathering surfactants, and mixtures thereof. Nonlimiting examples of lathering surfactants useful in the compositions of the present invention are disclosed in U.S. Pat. No. 6,280,757, to McAtee et al., issued Aug. 28, 2001. Generally, the lathering surfactants do not strongly interfere with deposition of any conditioning agents that are present, e.g., are fairly water soluble, and usually have an HLB value of above 10. Cationic surfactants can also be used as optional components, provided they do not negatively impact the overall lathering characteristics of the required lathering surfactants.

Anionic Lathering Surfactants

Nonlimiting examples of anionic lathering surfactants useful in the compositions of the present invention are disclosed in McCutcheon's, Detergents and Emulsifiers, North American edition (1986), published by allured Publishing Corporation; McCutcheon's, Functional Materials, North American Edition (1992); and U.S. Pat. No. 3,929,678, to Laughlin et al., issued Dec. 30, 1975.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates, and mixtures thereof. Amongst the isethionates, the alkoyl isethionates are preferred, and amongst the sulfates, the alkyl and alkyl ether sulfates are preferred.

Other anionic materials useful herein are soaps (i.e., alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl sarcosinate, sodium cocoyl sarcosinate, sodium myristoyl sarcosinate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, Detergents and Emulsifiers, North American edition (1986), published by allured Publishing Corporation; and McCutcheon's, Functional Materials, North American Edition (1992).

Nonionic lathering surfactants useful herein include those selected from the group consisting of alkyl glucosides, alkyl polyglucosides, polyhydroxy fatty acid amides, alkoxylated fatty acid esters, lathering sucrose esters, amine oxides, and mixtures thereof.

Nonlimiting examples of preferred nonionic surfactants for use herein are those selected form the group consisting of $C_8$-$C_{14}$ glucose amides, $C_8$-$C_{14}$ alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, Detergents and Emulsifiers, North American edition (1986), published by allured Publishing Corporation; and McCutcheon's, Functional Materials, North American Edition (1992).

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isetlionate, sodium cetyl sulfate, sodium lauroyl lactylate, triethanolamine lauroyl lactylate, and mixtures thereof, wherein the nonionic lathering surfactant is selected from the group consisting of lauramine oxide, cocoamine oxide, decyl polyglucose, lauryl polyglucose, sucrose cocoate, $C_{12\text{-}14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

Lather Volume Test

The articles of the present invention preferably comprise enough of the lathering surfactant such that the articles are capable of generating greater than or equal to about 30 ml, more preferably greater than or equal to about 50 ml, even more preferably greater than or equal to about 75 ml, and most preferably greater than or equal to about 150 ml of Average Lather Volume. The Average Lather Volume is a measurement determined by the Lather Volume Test. This test provides a consistent measurement of the volume of lather/foam generated by the articles described herein. The Lather Volume Test protocol is described as follows:

(1) Hands are washed with Ivory bar before conducting the test. This step removes any soils which may affect the accuracy of the measurement.

(2) The test article is held open in the non-dominant hand with the edges turned up.

(3) 10 ml. of water (medium hardness of about 8-10 grains per gallon) at 35° C. (95° F.) is added onto the test article via a 10 cc syringe or a Brinkmann repipetter.

(4) The lather is then generated by rubbing the test article with the dominant hand in a circular motion between the palms for 6 seconds (~2 rotations per second), using moderate pressure (e.g., 4 oz.), and allowing the article to ball-up between the palms of the hand.

(5) The test article is then held open in the non-dominant hand and an additional 10 ml of water (medium hardness of about 8-10 grains per gallon) at 35° C. (95° F.) is added onto the test article via a 10 cc syringe or a Brinkmann repipetter. The wetted article is again rubbed with the dominant hand (3 rotations) using moderate force (e.g, 4 oz.) so that the test article becomes balled-up between the palms.

(6) The test article is then opened and rubbed 5 times by holding one edge of the article in one hand and rotating the hand holding the other side to further activate lather.

(7) The test article is then flipped over and Step #6 is repeated using the other hand.

(8) The lather is gathered by holding the test article in a cupped hand and scraping the lather off the test article with the other hand, being careful to only scrape lather from the test article. The lather from the test article is placed into a graduated cylinder or beaker big enough to hold the generated lather. This procedure is repeated 5 times on the same test article, and the lather from each iteration is accumulated in the same graduated cylinder or beaker. The total accumulated lather from these iterations is designated as the Lather Volume.

(9) To achieve consistent results, the Average Lather Volume is reported as the average of three test sample replications of Steps 1-8.

Conditioning Component

The articles of the present invention will preferably further comprise a conditioning component which is useful for providing a conditioning benefit to the skin or hair during the use of the article. The conditioning component can comprise from about 0.05% to about 99%, preferably from about 0.1% to about 50%, and more preferably from about 1% to about 25% by weight of said water insoluble substrate.

The conditioning component useful in the present invention can comprise: a water soluble conditioning agent; an oil soluble conditioning agent; a conditioning emulsion; or any combination or permutation of the three. The oil soluble conditioning agent is selected from one or more oil soluble conditioning agents such that the weighted arithmetic mean solubility parameter of the oil soluble conditioning agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e., less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e., greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process.

Nonlimiting examples of conditioning agents useful as conditioning agents include those selected from the group consisting of fatty acids, esters of fatty acids, fatty alcohols, ethoxylated alcohols, polyol polyesters, glycerine, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, nonionic polymers, natural waxes, synthetic waxes, polyolefinic glycols, polyolefinic monoester, polyolefinic polyesters, cholesterols, cholesterol esters and mixtures thereof.

More particularly, the conditioning agent may be selected from the group consisting of paraffin, mineral oil, petrolatum, stearyl alcohol, cetyl alcohol, cetearyl alcohol, behenyl alcohol, C10-30 polyesters of sucrose, stearic acid, palmitic acid, behenic acid, oleic acid, linoleic acid, myristic acid, lauric acid, ricinoleic acid, steareth-1-100, cetereath 1-100, cholesterols, cholesterol esters, glyceryl tribehenate, glyceryl dipalmitate, glyceryl monostearate, trihydroxystearin, ozokerite wax, jojoba wax, lanolin wax, ethylene glycol distearate, candelilla wax, carnauba wax, beeswax, and silicone waxes.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415-417 (1993).

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36-37, 76, 78-80, 82 (1961); and International Cosmetic Ingredient Dictionary, Fifth Edition, vol. 1, p. 537 (1993).

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991.

The conditioning component preferably used in the present invention may also comprise a conditioning emulsion which is useful for providing a conditioning benefit to the skin or hair during the use of the article. The term "conditioning emulsion" as used herein means the combination of an internal phase comprising a water soluble conditioning agent that is enveloped by an external phase comprising an oil soluble agent. In preferred embodiments, the conditioning emulsion would further comprise an emulsifier. The conditioning emulsion comprises from about 0.25% to about 150%, preferably from about 0.5% to about 100%, and more preferably from about 1% to about 50% by weight of said water insoluble substrate. By a conditioning emulsion is meant a combination of an internal phase comprising a water soluble conditioning agent that is enveloped by an external phase comprising an oil soluble agent. In preferred embodiments, the conditioning emulsion would further comprise an emulsifier.

The conditioning emulsion comprises (i) an internal phase comprising water soluble conditioning agents as described above, and (ii) an external phase comprising oil soluble agents as described hereinbefore in the oil soluble conditioning agent section or hereinafter in the "Materials Used to Increase Lipid Hardness Value" section. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

Preferred embodiments of the present invention which contain conditioning emulsions comprise an emulsifier capable of forming an emulsion of the internal and external phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from about 0.1% to about 20%, preferably from about 1% to about 10%, and more preferably from about 3% to about 6% by weight of the conditioning emulsion.

The emulsifiers useful in the present invention typically are oil soluble or miscible with the oil soluble external phase materials, especially at the temperature at which the lipid material melts. It also should have a relatively low HLB value. Emulsifiers suitable for use in the present invention have HLB values typically in the range of from about 1 to about 7 and can include mixtures of different emulsifiers. Preferably, these emulsifiers will have HLB values from about 1.5 to about 6, and more preferably from about 2 to about 5.

Other Optional Ingredients

The articles of the present invention can comprise a wide range of other optional components. These additional components should be pharmaceutically acceptable. The CTFA Cosmetic Ingredient Handbook, Second Edition, 1992, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

Process of Manufacture

The personal cleansing articles of the present invention can be manufactured by providing a water insoluble substrate material, applying to the substrate a non-fibrous polymeric raised area coating on at least one side of the substrate, applying a lathering surfactant to the substrate, and optionally applying a conditioning component to the substrate. The process of manufacture is especially unique in that the non-fibrous polymeric raised areas, lathering surfactant, and optional conditioning component are each applied in the same process line, in the same pass. In a preferred process of manufacture, the process comprises providing a water insoluble substrate, applying a lathering surfactant to the substrate, then coating the substrate with the non-fibrous polymeric raised areas, and then applying a conditioning component to the substrate, with each step occurring in the same process line, in the same pass.

The personal care cleansing articles of the present invention can be manufactured by separately or simultaneously adding onto or impregnating into a water-insoluble substrate a lathering surfactant and optionally a conditioning component. If necessary, the resulting article can then be dried. By "separately" is meant that the surfactants and conditioning agents can be added sequentially, in any order without first being combined together. By "simultaneously" is meant that the surfactants and conditioning agents can be added at the same time, with or without first being combined together.

The lathering surfactant and/or the conditioning component can be added onto or impregnated into the substrate using any means known to those skilled in the art. These components can be applied using various spraying, soaking, coating or dipping techniques. Excess surfactant and/or conditioning component should be removed (e.g., by a nipping process). Thereafter, the treated substrate should be dried by conventional means.

When water or moisture is used or present in the manufacturing process, the resulting treated substrate is then preferably dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

Preferably, upon wetting with water during use, the articles of the present invention are capable of generating an Average Lather Volume of greater than or equal to about 30 ml, more preferably greater than or equal to about 50 ml, even more preferably greater than or equal to about 75 ml, and most preferably greater than or equal to about 150 ml.

Methods of Cleansing and Conditioning the Skin or Hair

The present invention also relates to a method of cleansing and conditioning the skin or hair with a personal cleansing article of the present invention. These methods comprise the steps of wetting with water a substantially dry, disposable, single use personal cleansing article comprising a water insoluble substrate, a lathering surfactant, and optionally a conditioning component, and contacting the skin or hair with such wetted article. In further embodiments, the present invention is also useful for delivering various active ingredients to the skin or hair.

The articles of the present invention are intended to be wetted with water prior to use. The article is wetted by immersion in water or by placing it under a stream of water. Lather is generated from the article by mechanically agitating and/or deforming the article either prior to or during contact of the article with the skin or hair. Preferably, upon wetting, the articles of the present invention generate an Average Lather Volume of greater than or equal to about 30 ml, more preferably greater than or equal to about 50 ml, even more preferably greater than or equal to about 75 ml, and most preferably greater than or equal to about 150 ml. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

EXAMPLES

The following are non-limiting examples of the personal cleansing articles of the present invention. The following Compositions A-E are prepared and utilized in Examples 1-5 as described below. Each Phase of Compositions A-E is prepared using processes known in the art and added to the substrates according to the processes described in Examples 1-5 below.

| Chemical Composition | A Wt % | B Wt % | C Wt % | D Wt % | E Wt % |
|---|---|---|---|---|---|
| PHASE A | | | | | |
| Glycerin | — | 9.53 | 9.53 | — | 11.67 |
| Cocamidopropyl Hydroxysultaine | 11.75 | — | — | 17.37 | — |
| Cocamidopropyl Betaine | — | 6.29 | 6.29 | — | 7.70 |
| Sodium Lauroyl Sarcosinate | 11.75 | 6.29 | 6.29 | 17.37 | 7.70 |
| Decyl Glucoside | 11.75 | 6.29 | 6.29 | 17.37 | 7.70 |
| Butylene Glycol | 3.56 | 1.91 | 1.91 | 5.26 | 2.33 |
| PEG 14M | 1.78 | 0.95 | 0.95 | 2.63 | 1.17 |
| Polyquaternium-10 | 0.89 | 0.48 | 0.48 | 1.32 | 0.58 |
| Panthenol | 0.71 | 0.38 | 0.38 | 1.05 | 0.47 |
| Phenoxyethanol | 0.53 | 0.29 | 0.29 | 0.79 | 0.35 |
| Benzyl Alcohol | 0.53 | 0.29 | 0.29 | 0.79 | 0.35 |
| Methylparaben | 0.44 | 0.24 | 0.24 | 0.66 | 0.29 |
| Propylparaben | 0.27 | 0.14 | 0.14 | 0.39 | 0.18 |

-continued

| Chemical Composition | A Wt % | B Wt % | C Wt % | D Wt % | E Wt % |
|---|---|---|---|---|---|
| Disodium EDTA | 0.18 | 0.10 | 0.10 | 0.26 | 0.12 |
| Salicylic Acid | 0.15 | 0.12 | 0.12 | 0.22 | 0.15 |
| WitchHazel Extract | 0.01 | — | — | 0.02 | — |
| Niacinamide | 0.01 | — | — | 0.02 | — |
| Vitamin E Acetate | 0.01 | 0.01 | 0.01 | 0.02 | 0.01 |
| Ascobyl Glucoside | 0.01 | — | — | 0.02 | — |
| PHASE B | | | | | |
| Petrolatum | 32.36 | 47.65 | 47.65 | — | 58.35 |
| PHASE C | | | | | |
| Polyethylene Glycol 4600 | 17.48 | 14.29 | 14.29 | 25.84 | — |
| Beta CycloDextrin | 4.95 | 4.05 | 4.05 | 7.32 | — |
| Fragrance | 0.76 | 0.71 | 0.71 | 1.12 | 0.88 |
| Menthol | 0.12 | — | — | 0.17 | — |
| Amt. of Phase Added to Substrate | | | | | |
| Phase A (Before Drying) | 42 gsm | 37 gsm | 54 gsm | 42 gsm | 37 gsm |
| Phase B | 8.5 gsm | 17 gsm | N/A* | N/A | 17 gsg |
| Phase C | 6.8 gsm | 6.8 gsm | 6.8 gsm | 6.8 gsm | N/A |

*Phase B emulsified into Phase A before coating

Example 1

A nonwoven article was prepared using 55 gsm Jacob Holm (50% Rayon, 50% Polyethylene terphathalate, hydroentangled nonwoven) material. An aqueous solution of Phase A ingredients are coated onto the nonwoven with a slot coater. Subsequently the material is passed through an oven to remove water. At the exit of the oven the nonwoven is printed with a visually pleasing pattern (combination of small continuous raised areas in a pattern of dots (each having a surface area of about 0.8 mm$^2$) for cleansing and large continuous raised areas (as shown in FIG. 1, each having a surface area of from about 50 mm$^2$ to about 500 mm$^2$) for conditioning) with Vestoplast 703 (a polymer with a Shore A hardness of about 70 supplied from Degussa Corporation) using a Rototherm Hotmelt Gravure coater (Rototherm Corporation Redding Calif.) The gravure cylinder is engraved to a depth of 140 um. After polymer printing, the article is coated with Phase B materials using a Nordson Corporation Slot coater. And finally, Phase C ingredients added to the cloth again using a Nordson Slot coater. The coatings and polymer printing occur in a single pass through the line. Meaning that the nonwoven is unwound at the beginning of the procedure and rewound after the final coating step. The completed rolls are then converted using a PCMC Corporation Mermaid wipes making line.

Example 2

A nonwoven article was prepared using 50 gsm PGI (75% Tencel, 25% Polyethylene terphathalate, hydroentangled nonwoven) material. An aqueous solution of Phase A ingredients are coated onto the nonwoven with a slot coater. Subsequently the material is passed through an oven to remove water. At the exit of the oven the nonwoven is printed with a visually pleasing pattern (combination of small continuous raised areas in a pattern of squares (each having a surface area of 3 mm$^2$) for cleansing and large continuous raised areas (as shown in FIG. 1, each having a surface area of from about 50 mm$^2$ to about 500 mm$^2$) for conditioning) with Elvax 210 (a polymer with a Shore A hardness of about 60 supplied from Dupont Corporation) using a Rototherm Hotmelt Gravure coater (Rototherm Corporation Redding Calif.) The gravure cylinder is engraved to a depth of 100 um. After polymer printing, the article is coated with Phase B materials using a Nordson Corporation Slot coater. And finally, Phase C ingredients added to the cloth again using a Nordson Slot coater. The coatings and polymer printing occur in a single pass through the line. Meaning that the nonwoven is unwound at the beginning of the procedure and rewound after the final coating step. The completed rolls are then converted using a PCMC Corporation Mermaid wipes making line.

Example 3

A nonwoven article was prepared using 60 gsm Ahlstrom Big Dot (75% Tencel, 25% Polyethylene terphathalate, hydroentangled nonwoven) material. An aqueous solution of emulsified Phase A & Phase B ingredients are coated onto the nonwoven with a slot coater. For this example Phase A and B add-on rates are calculated as one. Subsequently the material is passed through an oven to remove water. At the exit of the oven the nonwoven is printed with a visually pleasing pattern (combination of small continuous raised areas in a pattern of squares (each having a surface area of 2 mm$^2$) for cleansing and large continuous raised areas (as shown in FIG. 1, each having a surface area of from about 50 mm to about 500 mm$^2$) for conditioning) with Escorene MV2528 (a polymer with a Shore A hardness of about 50 supplied from Exxon Mobile Corporation) using a Rototherm Hotmelt Gravure coater (Rototherm Corporation Redding Calif.) The gravure cylinder is engraved to a depth of 200 um. And finally, Phase C ingredients added to the cloth again using a Nordson Slot coater. The coatings and polymer printing occur in a single pass through the line. Meaning that the nonwoven is unwound at the beginning of the procedure and rewound after the final coating step. The completed rolls are then converted using a Bretting Corporation napkin folder.

Example 4

A nonwoven article was prepared using 65 gsm BBA (50% Tencel, 50% Polyethylene, hydroentangled nonwoven) material. An aqueous solution of Phase A ingredients are coated onto the nonwoven with a slot coater. Subsequently the material is passed through an oven to remove water. At the exit of the oven the nonwoven is printed with a visually pleasing pattern (combination of small continuous raised areas in a pattern of diamonds (each having a surface area of 1 mm$^2$) for cleansing and large continuous raised areas (as shown in FIG. 1, each having a surface area of from about 50 mm$^2$ to about 500 mm$^2$) for conditioning) with Elvax 210 (a polymer with a Shore A hardness of about 60 supplied from Dupont Corporation) using a Rototherm Hotmelt Gravure coater (Rototherm Corporation Redding Calif.) The gravure cylinder is engraved to a depth of 60 um. And finally, Phase C ingredients added to the cloth again using a Nordson Slot coater. The coatings and polymer printing occur in a single pass through the line. Meaning that the nonwoven is unwound at the beginning of the procedure and rewound after the final coating step. The completed rolls are then converted using a in house build wipes converting line that cuts, folds and imparts rounded corners on the product.

Example 5

A nonwoven article was prepared using 58 gsm Jacolb Holm (25% Tencel, 25% Rayon, 50% Polyethylene terphathalate, hydroentangled nonwoven) material. An aqueous solution of Phase A & Phase C ingredients are coated onto the nonwoven with a slot coater. Subsequently the material is passed through an oven to remove water. At the exit of the oven the nonwoven is printed with a visually pleasing pattern (combination of small continuous raised areas in a pattern of circular dots (each having a surface area of 3 mm$^2$) for cleansing and large continuous raised areas (as shown in FIG. 1, each having a surface area of from about 50 mm to about 500 mm$^2$) for conditioning) with Elvax 210 (a polymer with a Shore A hardness of about 60 supplied from Dupont Corporation) using a Rototherm Hotmelt Gravure coater (Rototherm Corporation Redding Calif.) The gravure cylinder is engraved to a depth of 150 um for the circular dots and 100 um for the large continuous raised areas. After polymer printing, the article is coated with Phase B materials using a Nordson Corporation Slot coater. And finally, Phase C ingredients added to the cloth again using a Nordson Slot coater. The coatings and polymer printing occur in a single pass through the line. Meaning that the nonwoven is unwound at the beginning of the procedure and rewound after the final coating step. The completed rolls are then converted using a PCMC Corporation Mermaid wipes making line.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A substantially dry personal cleansing article comprising:
   (a) a water-insoluble non-apertured substrate comprising non-fibrous polymeric raised areas printed on at least one surface of said water insoluble substrate, wherein said non-fibrous polymeric raised areas are formed of a polymeric material having a Shore A hardness of up to 80, and wherein said non-fibrous polymeric raised areas comprise a plurality of small continuous raised areas and a plurality of large continuous raised areas, and wherein each of said small continuous raised areas comprise a surface area of from about 0.1 mm$^2$ to about 10 mm$^2$ and each of said large continuous raised areas comprise a surface area of greater than 50 mm$^2$ to about 5000 mm$^2$;
   (b) from about 0.5% to about 250%, by weight of said substrate, of a lathering surfactant; and
   (c) from about 0.05% to about 99%, by weight of said substrate, of a conditioning component.

2. The article of claim 1, wherein said small continuous raised areas each have a surface area of from about 0.5 mm$^2$ to about 5 mm$^2$ and said large continuous raised areas each have a surface area about 15 mm$^2$ to about 1,000 mm$^2$.

3. The article of claim 1, wherein said non-fibrous polymeric raised areas have an average height of from about 0.1 mm to about 0.5 mm.

4. The article of claim 1, wherein said non-fibrous polymeric raised areas are applied to said surface of said water-insoluble substrate via a gravure coating process.

5. The article of claim 1, wherein said polymeric material has a Shore A hardness of from about 40 to about 80.

6. The article of claim 1, wherein said polymeric material comprises an ethylene vinyl acetate copolymer material.

7. The article of claim 1, wherein said polymeric material comprises a propene-rich amorphous poly-alpha-olefin material.

8. The article of claim 1, wherein said polymeric material comprises a colorant.

9. The article of claim 1, wherein said water-insoluble substrate is a nonwoven substrate.

10. The article of claim 1, wherein said water-insoluble substrate is a hydroentangled nonwoven substrate.

11. The article of claim 1, wherein said water-insoluble substrate has a basis weight of from about 15 to about 100 grams per square meter.

12. The article of claim 1, wherein said lathering surfactant is selected from the group consisting of anionic lathering surfactants, nonionic lathering surfactants, amphoteric lathering surfactants, and mixtures thereof.

13. The article of claim 1, wherein said substantially dry personal cleansing article can generate an Average Lather Volume of 30 ml or more.

14. The article of claim 1, wherein said conditioning component comprises a conditioning emulsion.

15. The article of claim 1, wherein said conditioning component comprises petrolatum.

16. A substantially dry personal cleansing article comprising:
   (a) a water-insoluble non-apertured substrate comprising non-fibrous polymeric raised areas on at least one surface of said water insoluble substrate, wherein said non-fibrous polymeric raised areas are formed of a polymeric material having a Shore A hardness of up to 80, and wherein said non-fibrous polymeric raised areas comprise a plurality of small continuous raised areas and a plurality of large continuous raised areas, and wherein each of said small continuous raised areas comprise a surface area of from about 0.1 mm² to about 10 mm² and each of said large continuous raised areas comprise a surface area of greater than 50 mm² to about 5000 mm²; and (b) from about 0.5% to about 250%, by weight of said substrate, of a lathering surfactant releasably associated with said substrate.

\* \* \* \* \*